US009240254B2

(12) United States Patent
Schueler et al.

(10) Patent No.: US 9,240,254 B2
(45) Date of Patent: Jan. 19, 2016

(54) SYSTEM AND METHOD FOR CHARACTERIZING A FILM BY X-RAY PHOTOELECTRON AND LOW-ENERGY X-RAY FLUORESCENCE SPECTROSCOPY

(75) Inventors: Bruno W. Schueler, San Jose, CA (US); David A. Reed, Belmont, CA (US); Jeffrey Thomas Fanton, Los Altos, CA (US); Rodney Smedt, Los Gatos, CA (US)

(73) Assignee: ReVera, Incorporated, Sunnyvale, CA (US)

( * ) Notice: Subject to any disclaimer, the term of this patent is extended or adjusted under 35 U.S.C. 154(b) by 1098 days.

(21) Appl. No.: 13/246,488

(22) Filed: Sep. 27, 2011

(65) Prior Publication Data

US 2013/0077742 A1 Mar. 28, 2013

(51) Int. Cl.
*G01N 23/223* (2006.01)
*G21K 1/00* (2006.01)
(Continued)

(52) U.S. Cl.
CPC ............... *G21K 1/06* (2013.01); *G01N 23/223* (2013.01); *G01N 23/2273* (2013.01); *G01N 2223/61* (2013.01); *G21K 2201/062* (2013.01); *G21K 2201/064* (2013.01)

(58) Field of Classification Search
CPC ............ G01N 23/223; G01N 23/2076; G01N 2223/61; G01N 23/2273; G01N 2223/076; G01N 2223/0766; G01N 23/06; G01N 23/066; G01N 23/16; G01N 23/083; G21K 1/06; G21K 2201/062; G21K 2201/064; H05G 2/003; H05G 2/005; A61B 6/482; A61B 6/032; A61B 6/4035; A61B 6/4241; A61B 6/4042; A61B 6/502; A61B 6/505; A61B 6/583; A61B 6/4291; A61B 6/481; A61B 6/06; A61B 6/542; A61B 6/025; A61B 6/107; A61B 6/4417; A61B 6/0414; A61B 6/4021; A61B 6/4488
USPC .................... 378/44, 45, 85, 83, 70, 144, 145
See application file for complete search history.

(56) References Cited

U.S. PATENT DOCUMENTS 5,008,908 A * 4/1991 Jach et al. ........................ 378/70
5,444,242 A 8/1995 Larson et al.
(Continued)

FOREIGN PATENT DOCUMENTS

EP 0 331 375 9/1989
EP 2 328 153 6/2011
(Continued)

OTHER PUBLICATIONS

Kirby, et al., "Oxygen Detection in Thin Silicon Dioxide Layers by Low Energy X-Ray Fluorescence Spectrometry," Submitted to Journal of Vacuum Science and Technology, SLAC-PUB-5734, Apr. 1993, 30 pgs.
(Continued)

*Primary Examiner* — Irakli Kiknadze
(74) *Attorney, Agent, or Firm* — Blakely Sokoloff Taylor Zafman LLP (57) ABSTRACT

Systems and methods for characterizing films by X-ray photoelectron spectroscopy (XPS) are disclosed. For example, a system for characterizing a film may include an X-ray source for generating an X-ray beam having an energy below the k-edge of silicon. A sample holder may be included for positioning a sample in a pathway of the X-ray beam. A first detector may be included for collecting an XPS signal generated by bombarding the sample with the X-ray beam. A second detector may be included for collecting an X-ray fluorescence (XRF) signal generated by bombarding the sample with the X-ray beam. Monitoring/estimation of the primary X-ray flux at the analysis site may be provided by X-ray flux detectors near and at the analysis site. Both XRF and XPS signals may be normalized to the (estimated) primary X-ray flux to enable film thickness or dose measurement without the need to employ signal intensity ratios.

16 Claims, 6 Drawing Sheets

(51) Int. Cl.
  *G21K 1/06* (2006.01)
  *G01N 23/227* (2006.01)

(56) References Cited

U.S. PATENT DOCUMENTS

| | | | | |
|---|---|---|---|---|
| 5,778,041 A * | 7/1998 | Chase | ............... | G01N 23/06 378/51 |
| 7,358,494 B1 | 4/2008 | Gao et al. | | |
| 7,929,667 B1 * | 4/2011 | Zhuang et al. | ............... | 378/119 |
| 2004/0247080 A1 * | 12/2004 | Feda | ............... | 378/101 |
| 2008/0137803 A1 * | 6/2008 | Wu | ............... | A61B 6/032 378/5 |
| 2008/0226025 A1 * | 9/2008 | Harding | ............... | G01N 23/223 378/44 |
| 2008/0279332 A1 | 11/2008 | Rieutord | | |
| 2009/0268877 A1 | 10/2009 | Schueler et al. | | |
| 2012/0087463 A1 * | 4/2012 | Greenberg | ............... | G01T 7/005 378/5 |

FOREIGN PATENT DOCUMENTS

| | | |
|---|---|---|
| JP | 04191646 | 7/1992 |
| JP | 2000-097889 | 4/2000 |

OTHER PUBLICATIONS

International Preliminary Report on Patentability dated Apr. 1, 2014, in International Patent Application No. PCT/US2012/056752.
International Search Report and Written Opinion of the International Searching Authority dated Mar. 13, 2013, in International Patent Application No. PCT/US2012/056752.
Partial Supplementary European Search Report from European Patent Application No. 12835618.5 mailed Mar. 18, 2015, 7 pgs.
Allsop, N. A. et al., "Indium sulfide buffer/CIGSSe interface engineering: Improved cell performance by the addition of zinc sulfide," ScienceDirect, Thin Solid Films 515 (2007) pp. 6068-6072.
Castle, J. E. "Simultaneous electron and x-ray analysis and its application in corrosion science," Journal of Vacuum Science & Technology A 1, 1013 (1983), pp. 1013-1020.
Castle, J. E. et al., "Simultaneous XRF and XPS Analysis," Surface and Interface Analysis, vol. 5, No. 5 (1983), pp. 193-198.
Extended European Search Report from European Patent Application No. 12835618.5 mailed Jun. 24, 2015, 12 pgs.
Hitchcock, A. P., et al., "Si K-edge and Ge K-edge X-ray absorption spectroscopy of the Si—Ge interface in $[(Si)_m(Ge)_n]_p$ atomic layer superlattices," Surface Science 291 (1993) 349-369.
Cerino, J., et al., "An Ultra-High-Vacuum *Double Crystal Monochromator* Beam Line for Studies in the Spectral Range 500-4000 eV," Nuclear Instruments and Methods 172 (1980) 227-236.

* cited by examiner

XPS measurement:

(i) $I(Al)_{XPS} \sim \text{Flux} \cdot (1 - e^{-T2/\lambda(Al\ in\ Al)})$ (ii) $I(Al)_{measured\ XPS} \sim I(Al)_{XPS} \cdot e^{-T1/\lambda(Al\ in\ TiN)}$ e.g., $\lambda(Al\ in\ TiN) \sim 3$ nm (with WMα)

XRF measurement:

(iii) $I(Al)_{XRF} \sim \text{Flux} \cdot T2$ (iv) $I(Al)_{measured\ XRF} \sim I(Al)_{XRF} \cdot e^{-T1/\lambda(Al\ K\alpha\ in\ TiN)} \sim I(Al)_{XRF}$ e.g., $\lambda(Al\ K\alpha\ in\ TiN) \sim 1000$ nm

SYSTEM AND METHOD FOR CHARACTERIZING A FILM BY X-RAY PHOTOELECTRON AND LOW-ENERGY X-RAY FLUORESCENCE SPECTROSCOPY

BACKGROUND

1) Field

Embodiments of the invention are in the field of X-ray photoelectron spectroscopy (XPS) Analysis and, in particular, systems and methods for characterizing films by XPS.

2) Description of Related Art

X-ray photoelectron spectroscopy (XPS) is a quantitative spectroscopic technique that measures the elemental composition, empirical formula, chemical state and electronic state of the elements that exist within a material. XPS spectra may be obtained by irradiating a material with a beam of X-rays while simultaneously measuring the kinetic energy and number of electrons that escape from the top, e.g., 1 to 10 nm of the material being analyzed. XPS analysis commonly employs monochromatic aluminum K$\alpha$ (AlK$\alpha$) X-rays, which may be generated by bombarding an aluminum anode surface with a focused electron beam. A fraction of the generated AlK$\alpha$ X-rays is then intercepted by a focusing monochromator and a narrow X-ray energy band is focused onto the analysis site on a sample surface. The X-ray flux of the AlK$\alpha$ X-rays at the sample surface depends on the electron beam current, the thickness and integrity of the aluminum anode surface, and crystal quality, size, and stability of the monochromator.

X-ray fluorescence (XRF) is the emission of characteristic "secondary" (or fluorescent) X-rays from a material that has been excited by bombarding with higher energy X-rays or gamma rays. The phenomenon is widely used for elemental analysis and chemical analysis, particularly in the investigation of metals, glass, ceramics and building materials, and for research in geochemistry, forensic science and archaeology.

XPS analysis and XRF analysis each have their own advantages and drawbacks as techniques for sample characterization. Thus, advances are needed in analyses based on XPS and/or XRF detection.

SUMMARY

Embodiments of the present invention pertain to systems and methods for characterizing films by X-ray photoelectron spectroscopy (XPS).

In an embodiment, a system for characterizing a film includes an X-ray source for generating an X-ray beam having an energy below the absorption edge (k-edge) of silicon. A sample holder is included for positioning a sample in a pathway of the X-ray beam. A first detector is included for collecting an XPS signal generated by bombarding the sample with the X-ray beam. A second detector is included for collecting an XRF signal generated by bombarding the sample with the X-ray beam.

In another embodiment, a method for characterizing a film having a metal or element species includes generating an X-ray beam having an energy below the absorption edge (k-edge) of silicon. A sample is positioned in a pathway of the X-ray beam. An XPS signal generated by bombarding the sample with the X-ray beam is collected. An XRF signal generated by bombarding the sample with the X-ray beam is also collected.

In another embodiment, a monochromator for focusing an X-ray beam having an energy below the absorption edge (k-edge) of silicon includes a layer of indium antimonide (InSb) disposed directly on and conformal with a substrate layer of glass.

In another embodiment, a monochromator for focusing an X-ray beam having an energy below the absorption edge (k-edge) of silicon includes a layer of indium antimonide (InSb) disposed on and conformal with a layer of silicon. The layer of silicon is disposed above and conformal with a substrate layer of glass.

In another embodiment, a system for characterizing a film includes an X-ray source for generating an X-ray beam having an energy below the absorption edge (k-edge) of silicon. A sample holder is included for positioning a sample in a pathway of the X-ray beam. A monochromator is positioned between the X-ray source and the sample holder and in the pathway of the X-ray beam. The monochromator includes a layer of indium antimonide (InSb) disposed on and conformal with a layer of silicon. The layer of silicon and InSb is disposed above and conformal with a substrate layer of glass having a suitable doubly curved shape, e.g., ellipsoidal or toroidal). In one such embodiment, the monochromator structure (e.g., InSb/Si/Substrate) provides point-to-point focusing of X-rays emitted from the X-ray source (e.g., an anode) into a monochromatic X-ray spot focused at the sample. A detector for collecting an XPS signal generated by bombarding the sample with the X-ray beam is also included.

DETAILED DESCRIPTION

Systems and methods for characterizing films by X-ray photoelectron spectroscopy (XPS) are described. In the following description, numerous specific details are set forth, such as calibration techniques and system arrangements, in order to provide a thorough understanding of embodiments of the present invention. It will be apparent to one skilled in the art that embodiments of the present invention may be practiced without these specific details. In other instances, well-known features such as entire semiconductor device stacks are not described in detail in order to not unnecessarily obscure embodiments of the present invention. Furthermore, it is to be understood that the various embodiments shown in the Figures are illustrative representations and are not necessarily drawn to scale.

Various electronic events may occur when a sample including a layer disposed above a substrate is bombarded with X-rays. For example, an electron may be released from the sample. X-ray photoemission may occur for an electron generated within the top, e.g., 10 nanometers of the sample. Most information from an XPS measurement is usually obtained near the surface since attenuation of the electron signal occurs as the electrons travel through material on their way out. For measurements deeper in the sample (e.g., 0.1->2 microns deep), X-ray fluorescence (XRF) may be used since XRF signals typically attenuate 1000 times less than XPS photoelectron signals and are thus less susceptible to effects of depth within a sample.

XPS analysis commonly employs monochromatic aluminum Kα (AlKα) X-rays, which may be generated by bombarding an aluminum anode surface with a focused electron beam. The Al-based X-rays are typically focused with a quartz crystal monochromator. XPS signals obtained from samples bombarded with such radiation are typically strong and therefore often provide very meaningful data. However, as mentioned above, XRF measurements may also be needed to obtain information from deeper within a sample or information that is largely independent of layer thickness or depth. AlKα X-rays could also be utilized as a primary source for X-ray fluorescence analysis. However, the AlKα X-ray energy (1486.7 eV) is too low to generate useable XRF signals from a number of technologically important materials, including Al, Hf, and Ta. It is therefore desirable to utilize primary X-rays of somewhat higher energy than AlKα. At the same time, it is desirable to keep the excitation energy below the absorption edge for Si Kα X-ray generation for XRF (and XPS) analysis, about 1840 eV. By doing so, we avoid swamping the XRF measurement with a silicon signal from the Si substrate. Another approach to minimizing the competition with the Si signal would be to use X-ray energies well above the Si absorption edge (W Kα at 59 keV, Mo Kα at 17.5 keV, Ag Kα at 22 keV, Cr Kα at 5.4 keV, Cu Kα at 8 keV). These X-ray energies do preferentially excite higher-energy XRF signals and enhance their detection (for example for Hf or Zr), but at the expense of light element XRF detection (such as Al, O, or N). The higher X-ray energies also lead to a substantial loss in XPS photoelectron emission cross section (detectable signal).

In accordance with an embodiment of the present invention, X-rays with an energy less than the absorbing edge of silicon are used for XPS measurements. By using X-rays with an energy below the absorbing edge of silicon, enhanced XRF measurements without silicon signal interference may be made while accessing a broader range of element coverage of relevant materials (i.e., Al and Hf). For example, in one embodiment, XPS measurements are made using tungsten-sourced (W Mα) X-rays. Both XPS and XRF measurements are collected and are used together to aid in characterization of the sample. In an embodiment, an indium antimonide (InSb) monochromator is used with a tungsten-based X-ray source. In one such embodiment, a monochromator composed of a thin crystalline InSb layer bonded to a curved substrate surface is employed. In another such embodiment, a bilayer monochromator of InSb disposed on a layer of silicon (Si) is used and is bonded to a curved surface. Monitoring/estimation of the primary X-ray flux at the analysis site may be provided by X-ray flux detectors near and at the analysis site. Both XRF and XPS signals may be normalized to the (estimated) primary X-ray flux to enable film thickness or dose measurement without the need to employ signal intensity ratios.

In an aspect of the present invention, a film measurement system includes both an XPS detector and an XRF detector. For example, FIG. 1 is an illustration representing a film measurement system having XPS and XRF detection capability, in accordance with an embodiment of the present invention.

Figure 1:
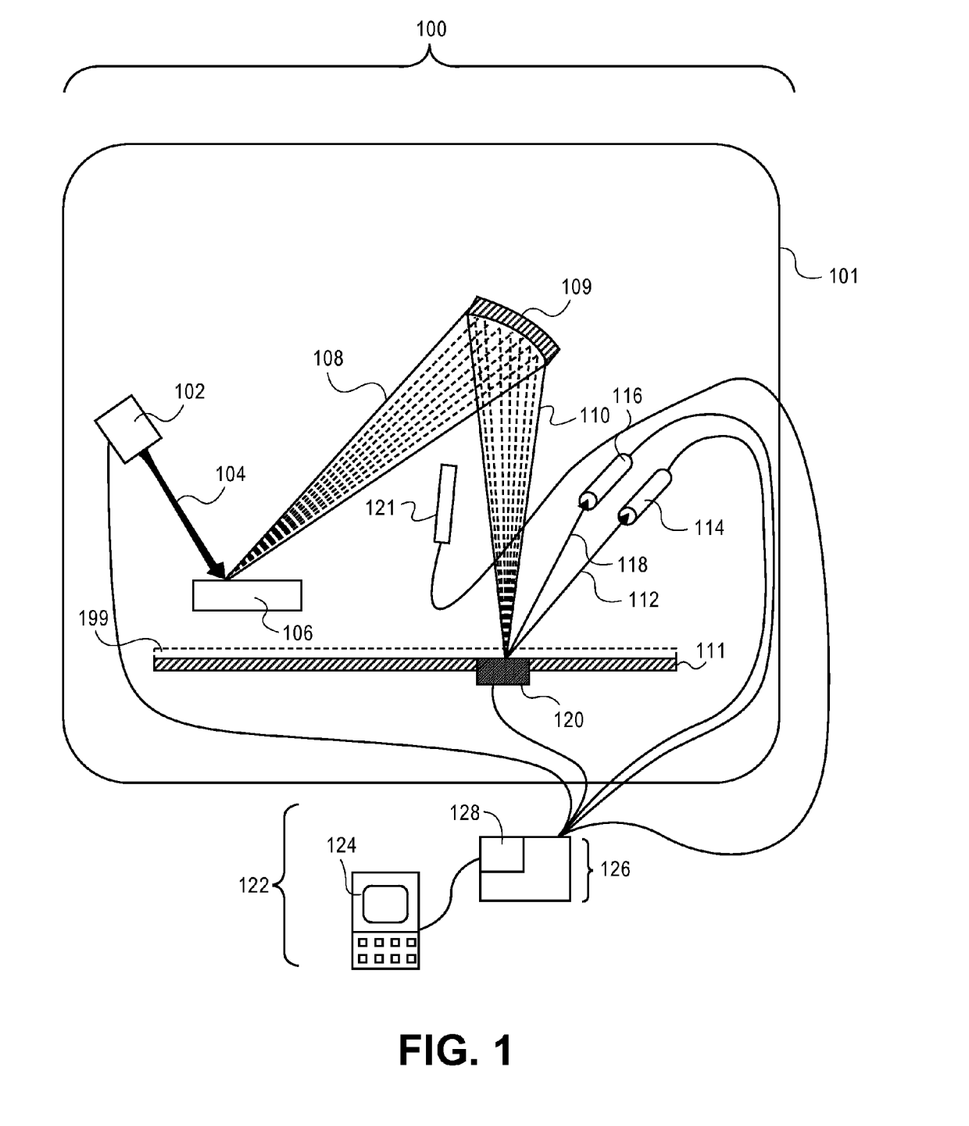
FIG. 1 is an illustration representing a film measurement system having XPS and XRF detection capability, in accordance with an embodiment of the present invention.

Referring to FIG. 1, a film measurement system 100 includes an XPS/XRF generation and detection system housed in a chamber 101 coupled with a computing system 122. The XPS/XRF generation and detection system includes an electron beam source 102 provided for generating an electron beam 104. Electron beam 104 is used to generate an X-ray beam 108 by bombarding an anode 106. A monochromator 109 is provided for transporting a monochromatized X-ray beam 110 from X-ray beam 108. A sample holder 111 may be used to position a sample 199 in a pathway of monochromatized X-ray beam 110.

An XPS detector 114 is provided for collecting an XPS signal 112 generated by bombarding sample 199 with monochromatized X-ray beam 110. An XRF detector 116 is provided for collecting an XRF signal 118 also generated by bombarding sample 199 with monochromatized X-ray beam 110. In an embodiment, system 100 is configured to collect XRF signal 118 and XPS signal 112 simultaneously or near simultaneously, representing single sampling event. The XPS signal 112 and XRF signal 118 are composed of photo-electrons and fluorescent X-rays, respectively. Additionally, a flux detector 120 may be provided for determining an estimated flux of monochromatized X-ray beam 110. In one such embodiment, flux detector 120 is positioned at sample holder 111, as depicted in FIG. 1. In another embodiment, an X-ray flux detector 121 is placed near the monochromator to partially intersect small fraction of the primary X-rays in order to monitor the X-ray flux while the sample holder 111 is positioned at the analysis site.

In an embodiment, X-ray beam 108 has an energy below the absorption edge (k-edge) of silicon. For example, in one embodiment, the energy is less than 1800 eV. In a particular embodiment, the anode 106 of FIG. 1 (e.g., the X-ray source) is or includes a tungsten (W) target. The W target may be used to provide a line below the silicon absorption edge (e.g., the M-line of tungsten). In an embodiment, by including a W target instead of, e.g., an aluminum (Al) target or molybdenum (Mo) target which provides a line in the absorption range of silicon, an XRF measurement taken on a non-silicon species on or above silicon may be greatly enhanced. However, the enhancement of the XRF signal may be obtained to some detriment of the quality of the XPS signal generated. That is, the signal strength of the XPS signal may be less for a W-target based X-ray beam versus an Al-target-based X-ray beam if generated under identical conditions. To overcome any such detriment to the XPS signal, in an embodiment, the W target is irradiated/heated by a higher current density electron beam to increase the flux of the X-ray beam generated from the target. It is possible to increase the current density on the W target, compared to a similar Al target, because of the higher melting point of W versus Al. Increased flux in turn leads to a stronger XPS signal. In an alternative embodiment, tantalum (Ta) is used in place of tungsten.

In an embodiment, the monochromator 109 is suitable for optimizing the focusing of an X-ray beam having an energy below the absorbing edge of silicon. For example, in one embodiment, the monochromator 109 is positioned between a tungsten X-ray source and the sample holder 111 and in the pathway of an X-ray beam generated from the tungsten source. In a particular such embodiment, the monochromator 109 is composed of a layer of indium antimonide (InSb) disposed on and conformal with a layer of silicon. The layer of silicon is disposed above and conformal with a substrate layer of glass of suitable shape and orientation to direct a monochromatic X-ray beam to the sample holder 111.

In accordance with an embodiment of the present invention, system 100 is configured to characterize a film. For example, since the X-ray beam 108 has an energy below the absorption edge (k-edge) of silicon, XPS and XRF measurements taken from a sample including a substantial amount of silicon, such as a silicon substrate, may be made with little to no interference or swamping by a silicon signal. In one embodiment, characterization of metal species in a film disposed on or above a silicon substrate is performed with high accuracy using an arrangement such as system 100.

In an embodiment, an XRF signal generated from system 100 is used to supplement the information of XPS signals generated from system 100 while referencing both XRF and XPS signals to the primary X-ray flux as measured with Flux detector 120 or 121. Computing system 122 includes a user interface 124 coupled with a computing portion 126 having a memory portion 128. Computing system 122 may be configured to calibrate an XPS signal detected by XPS detector 114. Computing system 122 may be configured to calibrate the XRF signal detected by XRF detector 116. Computing system 122 may be configured to monitor the primary X-ray flux as measured by Flux detector 120 and/or 121. In accordance with an embodiment of the present invention, computing system 322 is for normalizing an XPS signal detected by XPS detector 114, as well as an XRF signal detected by XRF detector 116 with the primary X-ray flux measured by Flux detector 120 or 121. In one embodiment, memory portion 328 has stored thereon a set of instructions for, when executed, using monochromatized X-ray beam 110 to generate XPS signal 112 and XRF signal 118 from sample 199.

Flux detector 120 may be used to determine an estimated flux of monochromatized X-ray beam 110. By positioning flux detector 120 at the point where monochromatized X-ray beam 110 meets sample holder 111, as depicted in FIG. 1, flux detector 120 may not be able to collect a portion of monochromatized X-ray beam 110 at the same time that sample 199 is in place on sample holder 111. Thus, in an embodiment, when flux detector 120 is positioned at the point where monochromatized X-ray beam 110 meets sample holder 111, an estimated flux of monochromatized X-ray beam 110 is determined when sample 199 is not present on sample holder 111. The flux is referred to as an 'estimated' flux, as opposed to a 'measured' flux which would be determined when a sample is actually present. In one embodiment, the estimated flux of the X-ray beam is obtained approximately immediately prior to generating the XPS signal from sample 199. In one embodiment, the estimated flux of the X-ray beam is obtained approximately immediately subsequent to generating the XPS signal from sample 199.

In an embodiment Flux detector 121 is used to provide a proxy X-ray flux measurement for Flux detector 120 for estimated flux of monochromatized X-ray beam 110. By positioning flux detector 121 at near the monochromator to intersect a small portion of the primary X-ray flux above the sample 111, the primary X-ray flux can be monitored while the monochromatized X-ray beam 110 meets sample holder 111, as depicted in FIG. 1, and while XPS and XRF signals 118 and 112 are recorded by XRF detector 116 and XPS detector 114.

In another aspect of the present invention, a monochromator is provided optimized for use with an X-ray beam having an energy below the absorption edge (k-edge) of silicon. For example, FIG. 2 illustrates a bottom-up view (2A), a cross-sectional view taken in the Y-direction (2B), and a cross-sectional view taken in the X-direction, of a monochromator, in accordance with an embodiment of the present invention.

Figure 2A:
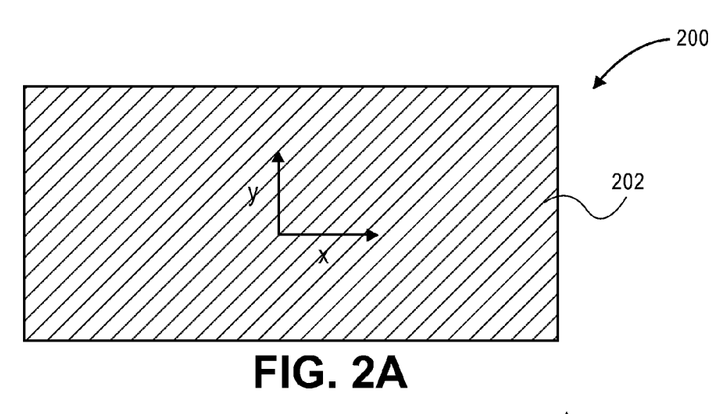
FIG. 2A illustrates a bottom-up view of a double curved monochromator, in accordance with an embodiment of the present invention.
Figure 2B:
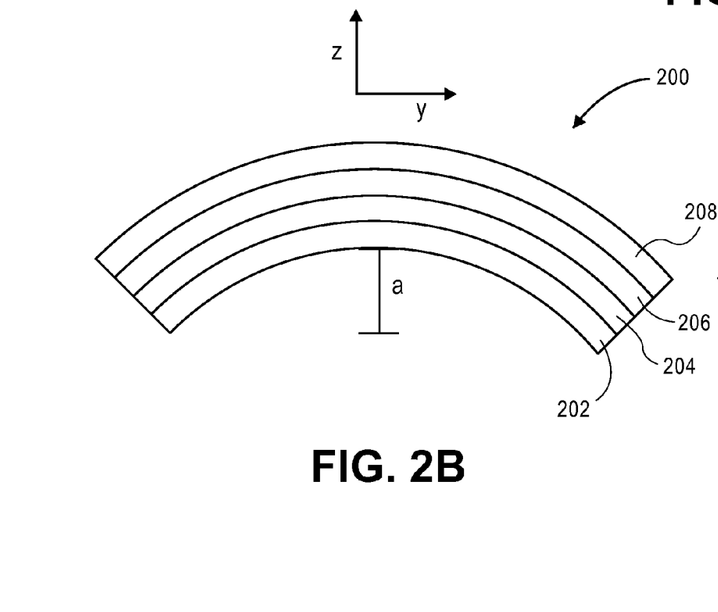
FIG. 2B illustrates a cross-sectional view taken in the Y-direction of a monochromator, in accordance with an embodiment of the present invention.
Figure 2C:
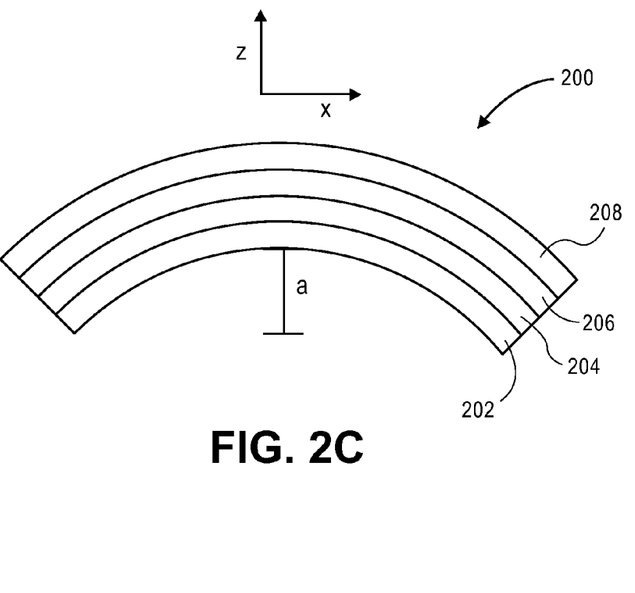
FIG. 2C illustrates a cross-sectional view taken in the X-direction of a monochromator, in accordance with an embodiment of the present invention.

Referring to FIGS. 2A-2C, a monochromator 200 includes a layer of indium antimonide (InSb) 202 disposed on and conformal with a layer of silicon 204. The layer of silicon 204 is disposed above and conformal with a layer of glass 208. However, in another embodiment, the layer of silicon 204 is omitted and the layer of InSb 202 is disposed directly on and conformal with the layer of glass 208. In an embodiment, the monochromator 200 is suitable for focusing an X-ray beam having an energy below the absorption edge (k-edge) of silicon. Such a pairing may permit more X-rays per unit of time (flux) as compared to coupling with a conventional monochromator such as a quartz monochromator. In a specific such embodiment, the monochromator is for focusing an X-ray beam generated from a tungsten (W) source.

In an embodiment, the substrate layer of glass 208 has a curved (ellipsoidal) shape, e.g., a curve in more than one dimension as would otherwise be the case for a cylindrical curve. For example, referring to FIGS. 2B and 2C, the monochromator 200 is displaced from a horizontal surface by an amount "a" in both the x-axis and the y-axis. In one such embodiment, the monochromator 200 has a latitudinal dimension (along the x-axis) approximately in the range of 1-5 centimeters, a longitudinal dimension (along the y-axis) approximately in the range of 3-15 centimeters. The latitudinal shape of the monochromator ellipsoid (minor axis) has to satisfy the Bragg condition and maintain a Bragg angle of approximately 68.9 degrees for InSb to deliver a monochromated W Mα X-ray beam to the sample 111. The longitudinal shape of the monochromator focusing ellipsoid is given by minor ellipsoid axis and corresponding distance of the ellipsoid foci via the well known ellipsoid focusing equation.

In one particular embodiment, the shape of the monochromator ellipsoid has a major ellipsoid axis of a approximately in the range of 9-12 centimeters, a minor ellipsoid axis of b approximately in the range of 8-11 centimeters and thus a spacing of the foci of 2x approximately 35-40 centimeters, using InSb (2d-lattice spacing of approximately 7.4812 and Bragg angle of approximately 68.91 degree) to monochromate and focus W Mα X-rays from the anode to the analysis spot on the sample 111. Alternate focusing configurations may be obtained as long as the Bragg angle for InSb, as well as the ratios b/a approximately in the range of 0.85-1.0 and c/b approximately in the range of 0.35-0.42 are satisfied.

In an embodiment, the monochromator 200 further includes an interfacial region 206 between the silicon layer 204 and the glass layer 208, as depicted in FIGS. 2B and 2C. The interfacial region 206 may enable bonding between the silicon layer 204 and the glass layer 208. In one such embodiment, the monochromator 200 includes the layer of InSb 202 having a thickness of approximately 5-15 microns, the layer of silicon 204 having a thickness less than 90 microns, the substrate layer of glass 208 having a thickness approximately in the range of 2-10 centimeters, and further includes an interfacial silicon dioxide ($SiO_2$) layer 206 disposed between the layer of silicon 204 and the layer of glass 208. The interfacial $SiO_2$ layer has a thickness approximately in the range of 50-150 nanometers. In a particular embodiment, if the layer of silicon 204 has a thickness greater than 90 microns, it may be brittle and break during coupling to the ellipsoidal surface of the glass substrate 208.

In an embodiment, the InSb layer 202 is first bonded to a flat silicon layer prior to forming the monochromator 202. Once the flat bonding is performed, the InSb/Si pairing is bonded to the appropriate ellipsoidal surface of the glass substrate layer 208. In one embodiment, the InSb/Si pairing may be replaced with a InSb/Ge pairing, which is subsequently bonded to the ellipsoidal glass substrate 208.

In another aspect of the present invention, an XPS system need not include XRF capability but may be arranged in a manner suitable for generating an X-ray beam having an energy below the absorption edge (k-edge) of silicon. For example, FIG. 3 is an illustration representing a film measurement system having XPS detection capability, in accordance with an embodiment of the present invention.

Figure 3:
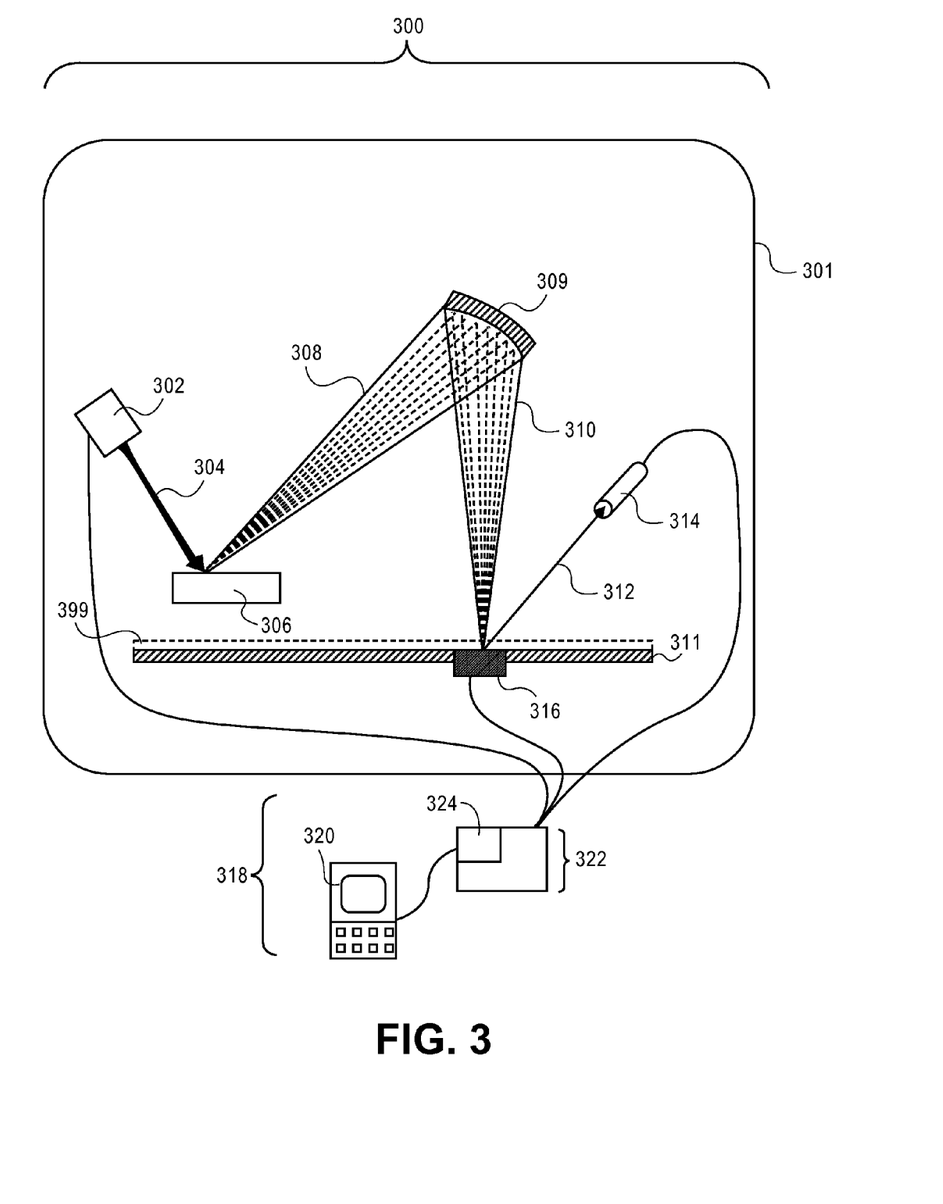
FIG. 3 is an illustration representing a film measurement system having XPS detection capability, in accordance with an embodiment of the present invention.

Referring to FIG. 3, a film measurement system 300 includes an XPS generation and detection system housed in a chamber 301 coupled with a computing system 318. The XPS generation and detection system includes an electron beam source 302 provided for generating an electron beam 304. Electron beam 304 is used to generate an X-ray beam 308 by bombarding an anode 306. A monochromator 309 is provided for focusing a monochromatized X-ray beam 310 from X-ray beam 308. A sample holder 311 may be used to position a sample 399 in a pathway of monochromatized X-ray beam 310.

An XPS detector 314 is provided for collecting an XPS signal 312 generated by bombarding sample 399 with monochromatized X-ray beam 310. Additionally, a flux detector 316 may be provided for determining an estimated flux of monochromatized X-ray beam 310. In one such embodiment, flux detector 316 is positioned at sample holder 311, as depicted in FIG. 3. Computing system 318 includes a user interface 320 coupled with a computing portion 322 having a memory portion 324.

In an embodiment, system 300 is for characterizing a metal-species-containing film and includes an X-ray source for generating an X-ray beam having an energy below the absorption edge (k-edge) of silicon. For example, in one embodiment, the energy is less than 1800 eV. In one embodiment, the X-ray source is or includes a tungsten (W) target. In an embodiment, the monochromator 309 is positioned between the X-ray source (e.g., anode 306) and the sample holder 311 and in the pathway of the X-ray beam 308, as depicted in FIG. 3. In one embodiment, the monochromator 309 includes a layer of indium antimonide (InSb) disposed on and conformal with an ellipsoidal glass substrate. In another embodiment, the monochromator 309 includes a layer of indium antimonide (InSb) disposed on and conformal with a layer of silicon. The layer of silicon is disposed above and conformal with an ellipsoidal glass substrate. Thus, in accordance with an embodiment of the present invention, an XPS system includes a tungsten (or the like) target for generating an X-ray beam with an energy below the absorption edge of silicon, and also includes a InSb-based monochromator particular suited from focusing such lower energy X-ray beams, such as W Mα, onto a sample for analysis.

In an aspect of the invention, an XPS measurement may be made upon introduction of a sample into an XPS system, such as but not limited to XPS systems 100 and 300. In accordance with an embodiment of the present invention, the sample is bombarded with an X-ray beam. In response to bombardment by the X-ray beam, and XPS signal (composed of photoelectrons) may be emitted from the sample and collected in a detector. In an embodiment, the XPS signal is correlated with the atomic dose of a particular atomic species in the sample. In one embodiment, the atomic dose is correlated with a sample property such as, but not limited to, the thickness of a film in the sample, the depth to which the particular atomic species is incorporated into the sample or a concentration ratio of several atomic species in the sample. Additionally, one or more of the species may be a metal species. For example, in a particular embodiment, an XPS signal for a dielectric layer such as, but not limited to, silicon dioxide, silicon oxy-nitride, aluminum oxide or hafnium oxide, is obtained. In accordance with an embodiment of the present invention, the XPS signal is correlated to a property of the dielectric film without having to obtain, reference or ratio an XPS signal of, e.g., an underlying substrate or reference film. In one embodiment, the XPS signal is calibrated with a simultaneously or near simultaneously collected XRF signal, as well as the estimated X-ray flux recorded by X-ray Flux detectors 120 or 121.

Figure 4:
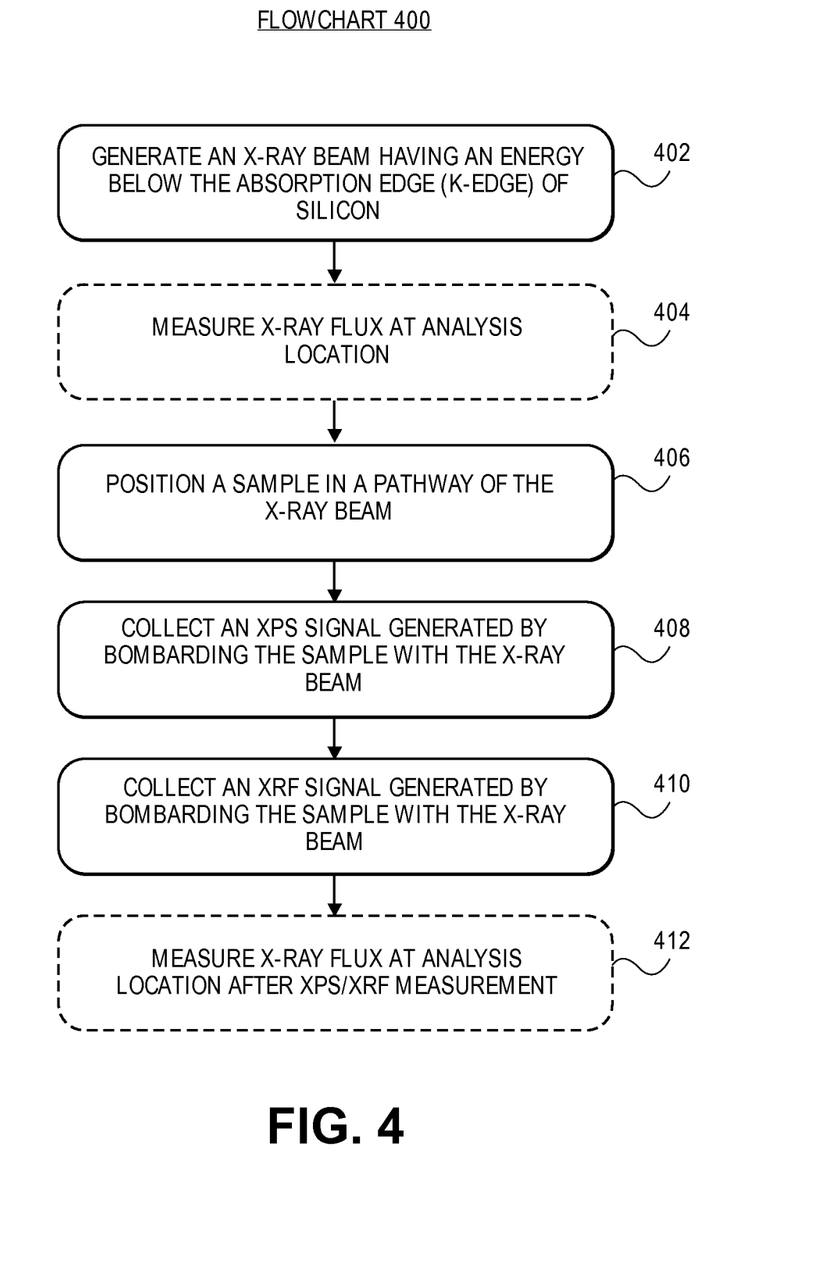
FIG. 4 is a Flowchart representing a series of operations in a method for characterizing a film, in accordance with an embodiment of the present invention.
Figure 5A:
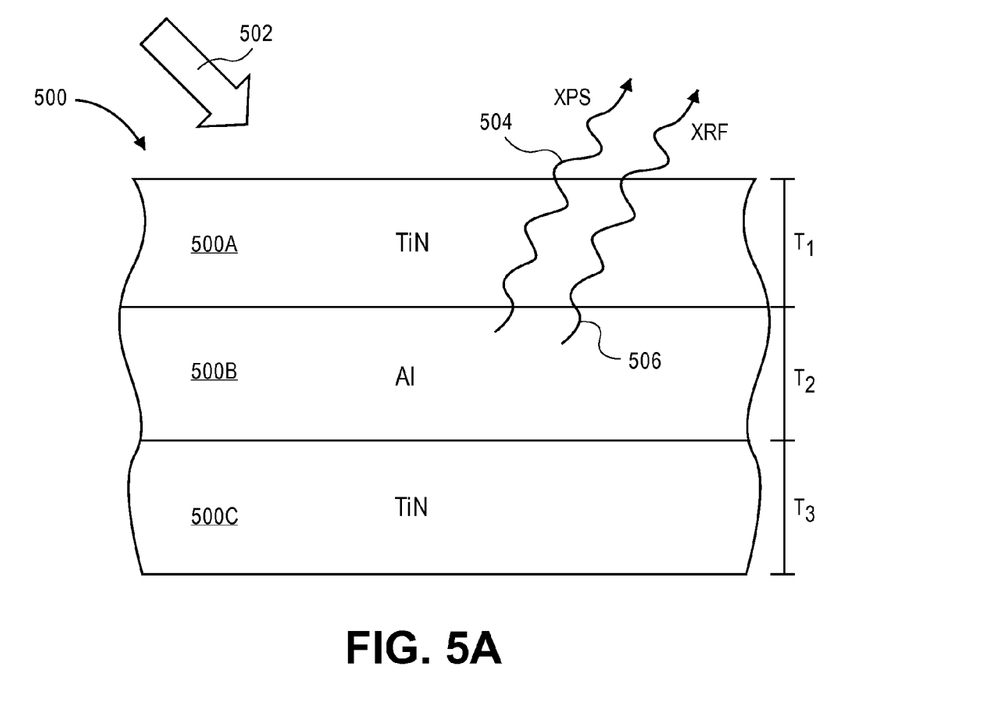
FIG. 5A illustrates a cross-sectional view of a sample including metal species for characterization by XPS and XRF, in accordance with an embodiment of the present invention.
Figure 5B:
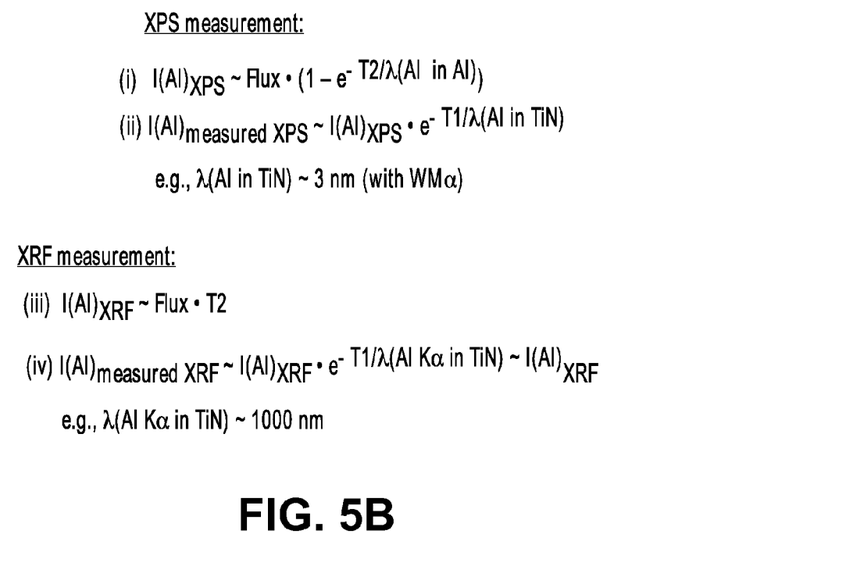
FIG. 5B includes equations used for analysis of XPS and XRF signals emitted from the sample of FIG. 5A, in accordance with an embodiment of the present invention.

In an aspect of the present invention, as described briefly above, an XRF measurement may be used to glean additional information from an XPS measurement made from a sample. The sample may include a metal species of other element species such as oxygen or nitrogen. For example, FIG. 4 is a Flowchart 400 representing a series of operations in a method for characterizing a film, in accordance with an embodiment of the present invention. FIG. 5A illustrates a cross-sectional view of a sample including metal species for characterization by XPS and XRF. FIG. 5B includes equations used for analysis of XPS and XRF signals emitted from the sample of FIG. 5A.

Referring to operation 402 of Flowchart 400 and to corresponding FIG. 5A, a method for characterizing a film includes generating an X-ray beam 502 having an energy below the absorption edge (k-edge) of silicon. In an embodiment, generating the X-ray beam 502 has an energy less than 1800 eV. In an embodiment, the X-ray beam 502 is generated from a tungsten (W) target. In an embodiment, the film includes one or more metal species such as, but not limited to, hafnium, aluminum, lanthanum or titanium. In another embodiment, the film includes oxygen or nitrogen.

Referring to operation 404 of Flowchart 400 and to corresponding FIG. 5A, the method optionally also includes positioning an X-ray Flux detector (e.g., X-ray Flux detector 120 from FIG. 1) in the pathway of the X-ray beam 502. The X-ray flux is measured prior to placing the sample 500 in a pathway of the X-ray beam 502. In an alternative implementation, an X-ray flux detector (e.g., X-ray flux detector 121 from FIG. 1) may be used to monitor the X-ray flux stability during XPS and XRF measurements while the sample 500 is placed in a pathway of the X-ray beam 502. The X-ray flux measurement serves as reference for the measured XPS 504 and XRF 506 signal intensities. Both the XPS and the XRF signal intensity are directly proportional to the primary X-ray flux (120 or 121) for a given sample structure and measurement configuration. Normalization of measured XRF and XPS intensities by the X-ray flux permits thickness/dose measurement without the need for XRF or XPS signal intensity ratios (as is commonly used in XPS analysis).

Referring to operation 406 of Flowchart 400 and to corresponding FIG. 5A, the method also includes positioning a sample 500 in a pathway of the X-ray beam 502. In an embodiment, the sample 500 includes one or more films having metal species. For example, in a specific embodiment, the sample 500 includes a first layer of titanium nitride (TiN) 500A having thickness T1 disposed above a layer including aluminum (Al) 500B having thickness T2 which, in turn, is disposed above a second layer of titanium nitride (TiN) 500C having thickness T3, as depicted in FIG. 5A. The stack of layers 500A, 500B, 500C is disposed on or above a silicon substrate.

Referring to operation 408 of Flowchart 400 and to corresponding FIG. 5A, the method also includes collecting an XPS signal 504 generated by bombarding the sample 500 with the X-ray beam 502. For example, an XPS signal 504 obtained from the layer including aluminum (Al) 500B may be collected, as depicted in FIG. 5A. An XPS spectra may be obtained by irradiating the sample 500 with a beam of X-rays 502 while simultaneously measuring the kinetic energy and number of electrons that escape from the top, e.g., 1 to 10 nm of the sample 500.

Referring to operation 410 of Flowchart 400 and to corresponding FIG. 5A, the method also includes collecting an XRF signal 506 generated by bombarding the sample 500 with the X-ray beam 502. For example, an XRF signal 506 obtained from the layer including aluminum (Al) 500B may be collected, as depicted in FIG. 5A. An XRF spectra may be obtained may be obtained by irradiating the sample 500 with a beam of X-rays 502 and measuring the emission of characteristic secondary (or fluorescent) X-rays there from. Referring to operation 412, in an embodiment, the method optionally further includes performing a Flux measurement following completion of the above analysis.

In an embodiment, the method further includes combining the measurement result from the XPS signal 504 and the XRF signal 506. In a specific example, a repeating layer structure may be used as a sample, such as the repeating layer structure 500 which includes more than one layer of titanium nitride. Referring to FIG. 5A and equations (i) and (ii) of FIG. 5B, the intensity (I(Al)) of the XPS signal 504 generated from layer 500B (having thickness T2) is attenuated by layer 500A based on the thickness (t, or T1) of layer 500A and the photoelectron attenuation length associated with the Al signal 504 ($\lambda$Al). On the other hand, since the XRF signal 506 is largely not depth dependent at or below the 100 nm scale, the signal is not attenuated. Accordingly, the XRF signal 506 may be used to determine an amount of aluminum present in sample 500. The amount of aluminum I(Al) determined from XRF signal 506 may be used in equation (iv) of FIG. 5B along with the measured XPS signal 504 (I measured) to determine the thickness (t, or T1) of the top titanium nitride layer. That is, the XRF signal 506, which provides an amount of aluminum present (equation (iii)), may be used to determine the depth of the aluminum, which directly corresponds to the thickness (T1) of the titanium nitride layer 500A and the thickness (T2) of the aluminum containing layer 500B. XRF (and XPS) measurement of the Ti signal yields the total TiN thickness of the stack (T1+T3). The thickness of TiN layer (T3) thus follows directly, as the top TiN layer thickness (T1) has already been determined from XPS and XRF measurements of the respective Al signal intensities.

Thus, in accordance with an embodiment of the present invention, a method further includes determining, for a film including the metal species disposed below one or more other films, and the XPS signal having an attenuated signal intensity of the metal species, and an XRF signal having an essentially non-attenuated signal of the metal species. In one such embodiment, calibrating the XPS signal to the XRF signal includes determining a quantity of the metal species from the XRF signal and, subsequently, determining, from the XPS signal and the quantity, a depth of the film below the one or more other films.

In another, alternative embodiment, a method further includes calibrating the XPS signal with the XRF signal for the very top film of a stack of films on a silicon substrate. In one such example, a quantity of the metal (or atomic element) species is determined from the XRF signal (normalized to the X-ray flux) and, subsequently, a thickness of the top film including the metal species is determined from the XPS signal and the quantity provided by the XRF measurement. This approach may provide for ease of XPS calibration for new film materials, particularly if the XRF signal is normalized to the X-ray flux.

Embodiments of the present invention may be provided as a computer program product, or software, that may include a machine-readable medium having stored thereon instructions, which may be used to program a computer system (or other electronic devices) to perform a process according to the present invention. A machine-readable medium includes any mechanism for storing or transmitting information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices, etc.), a machine (e.g., computer) readable transmission medium (electrical, optical, acoustical or other form of propagated signals (e.g., infrared signals, digital signals, etc.)), etc.

Figure 6:
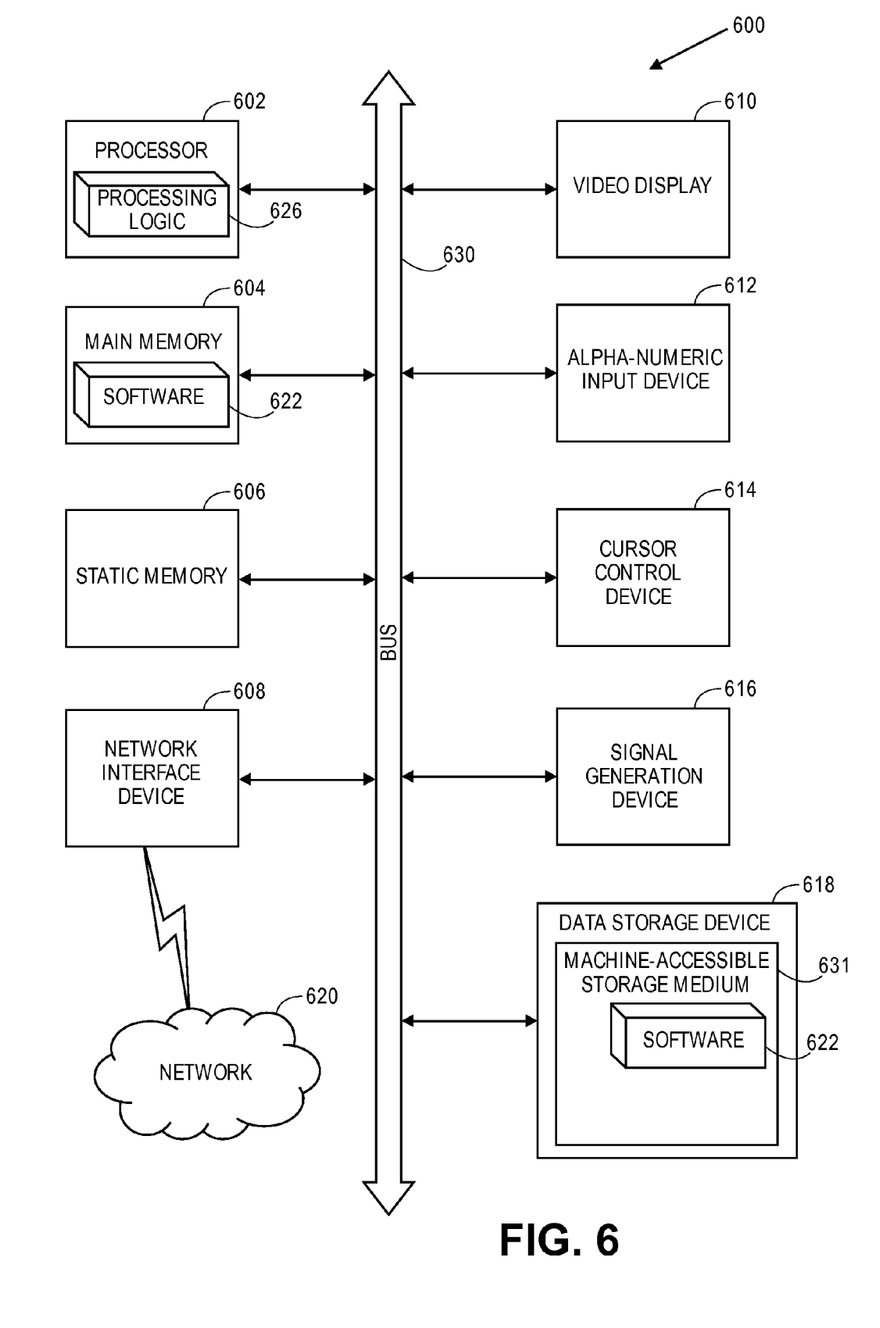
FIG. 6 illustrates a block diagram of an exemplary computer system, in accordance with an embodiment of the present invention.

FIG. 6 illustrates a diagrammatic representation of a machine in the exemplary form of a computer system 600 within which a set of instructions, for causing the machine to perform any one or more of the methodologies discussed herein, may be executed. In alternative embodiments, the machine may be connected (e.g., networked) to other machines in a Local Area Network (LAN), an intranet, an extranet, or the Internet. The machine may operate in the capacity of a server or a client machine in a client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines (e.g., computers) that individually or jointly execute a set (or multiple sets) of instructions to perform any one or more of the methodologies discussed herein. For example, in an embodiment, a machine is configured to execute one or more sets of instruction for calibrating an XPS signal measurement with an XRF signal measurement.

The exemplary computer system 600 includes a processor 602, a main memory 604 (e.g., read-only memory (ROM), flash memory, dynamic random access memory (DRAM) such as synchronous DRAM (SDRAM) or Rambus DRAM (RDRAM), etc.), a static memory 606 (e.g., flash memory, static random access memory (SRAM), etc.), and a secondary memory 618 (e.g., a data storage device), which communicate with each other via a bus 630.

Processor 602 represents one or more general-purpose processing devices such as a microprocessor, central processing unit, or the like. More particularly, the processor 602 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processor 602 may also be one or more special-purpose processing devices such as an application specific integrated circuit (ASIC), a field programmable gate array (FPGA), a digital signal processor (DSP), network processor, or the like. Processor 602 is configured to execute the processing logic 626 for performing the operations discussed herein.

The computer system 600 may further include a network interface device 608. The computer system 600 also may include a video display unit 610 (e.g., a liquid crystal display (LCD) or a cathode ray tube (CRT)), an alphanumeric input device 612 (e.g., a keyboard), a cursor control device 614 (e.g., a mouse), and a signal generation device 616 (e.g., a speaker).

The secondary memory 618 may include a machine-accessible storage medium (or more specifically a computer-readable storage medium) 631 on which is stored one or more sets of instructions (e.g., software 622) embodying any one or more of the methodologies or functions described herein. The software 622 may also reside, completely or at least partially, within the main memory 604 and/or within the processor 602 during execution thereof by the computer system 600, the main memory 604 and the processor 602 also constituting machine-readable storage media. The software 622 may further be transmitted or received over a network 620 via the network interface device 608.

While the machine-accessible storage medium 631 is shown in an exemplary embodiment to be a single medium, the term "machine-readable storage medium" should be taken to include a single medium or multiple media (e.g., a centralized or distributed database, and/or associated caches and servers) that store the one or more sets of instructions. The term "machine-readable storage medium" shall also be taken to include any medium that is capable of storing or encoding a set of instructions for execution by the machine and that cause the machine to perform any one or more of the methodologies of the present invention. The term "machine-readable storage medium" shall be taken accordingly to include, but not be limited to, solid-state memories, and optical and magnetic media.

Thus, systems and methods for characterizing films by XPS have been described. In accordance with an embodiment of the present invention, a system for characterizing a film includes an X-ray source for generating an X-ray beam having an energy below the absorption edge (k-edge) of silicon. The system also includes a sample holder for positioning a sample in a pathway of the X-ray beam. The system also includes a first detector for collecting an XPS signal generated by bombarding the sample with the X-ray beam. The system also includes a second detector for collecting an XRF signal generated by bombarding the sample with the X-ray beam. In one embodiment, the X-ray source includes a tungsten (W) target. In one embodiment, the XRF signal is for calibrating the XPS signal.

What is claimed is:

1. A system for characterizing a film, said system comprising:
   an X-ray source for generating an X-ray beam having an energy below the absorption edge (k-edge) of silicon;
   a sample holder for positioning a sample in a pathway of said X-ray beam;
   a first detector for collecting an X-ray photoelectron spectroscopy (XPS) signal generated by bombarding said sample with said X-ray beam; and
   a second detector for collecting an X-ray fluorescence (XRF) signal generated by bombarding said sample with said X-ray beam.

2. The system of claim 1, further comprising:
   a third detector for monitoring a primary X-ray flux to said sample.

3. The system of claim 1, wherein said energy is less than 1800 eV.

4. The system of claim 3, wherein said X-ray source comprises a tungsten (W) target.

5. The system of claim 1, further comprising:
   a monochromator positioned between said X-ray source and said sample holder and in said pathway of said X-ray beam.

6. The system of claim 5, wherein said monochromator comprises a layer of indium antimonide (InSb) disposed on and conformal with a glass substrate having an ellipsoidal shape.

7. The system of claim 5, wherein said monochromator comprises a layer of indium antimonide (InSb) disposed on and conformal with a layer of silicon, said layer of silicon disposed above and conformal with a glass substrate having an ellipsoidal shape.

8. The system of claim 1, wherein said XRF signal is for calibrating said XPS signal.

9. The system of claim 1, wherein said system is configured to characterize a film comprising a metal species.

10. A method for characterizing a film comprising a metal or atomic element species, said method comprising:
    generating an X-ray beam having an energy below the absorption edge (k-edge) of silicon;
    positioning a sample in a pathway of said X-ray beam;
    collecting an X-ray photoelectron spectroscopy (XPS) signal generated by bombarding said sample with said X-ray beam; and
    collecting an X-ray fluorescence (XRF) signal generated by bombarding said sample with said X-ray beam.

11. The method of claim 10, further comprising:
    calibrating said XPS signal with said XRF signal.

12. The method of claim 11, wherein said film comprising said metal or atomic element species is disposed below one or more other films, wherein said XPS signal comprises and attenuated intensity signal of said metal or atomic element species, and wherein said XRF signal comprises a non-attenuated signal of said metal or atomic element species.

13. The method of claim 12, wherein calibrating said XPS signal with said XRF signal comprises:
    determining a quantity of said metal or atomic element species from said XRF signal; and, subsequently,
    determining, from said XPS signal and said quantity, a depth of said film below said one or more other films.

14. The method of claim 11, wherein calibrating said XPS signal with said XRF signal comprises:
    determining a quantity of said metal or atomic element species from said XRF signal; and, subsequently,
    determining a thickness of said film comprising said metal or atomic element species from said XPS signal and said quantity.

15. The method of claim 10, wherein generating said X-ray beam having an energy below the absorption edge (k-edge) of silicon comprises generating an X-ray beam having an energy less than 1800 eV.

16. The method of claim 10, wherein characterizing said film comprising said metal or atomic element species comprises characterizing a film comprising a metal or atomic element species selected from the group consisting of hafnium, aluminum, lanthanum, titanium, tantalum, nitrogen, and oxygen.

* * * * *